(12) United States Patent
Carrero

(10) Patent No.: US 10,004,629 B1
(45) Date of Patent: Jun. 26, 2018

(54) OSTOMY BAG WITH GAS CHECK VALVE AND WATER BOTTLE CONNECTION

(71) Applicant: Brandon Carrero, Miramar, FL (US)

(72) Inventor: Brandon Carrero, Miramar, FL (US)

( * ) Notice: Subject to any disclaimer, the term of this patent is extended or adjusted under 35 U.S.C. 154(b) by 676 days.

(21) Appl. No.: 14/623,929

(22) Filed: Feb. 17, 2015

(51) Int. Cl.
*A61F 5/441* (2006.01)
*A61F 5/442* (2006.01)
*A61F 5/44* (2006.01)
*A61F 5/448* (2006.01)

(52) U.S. Cl.
CPC .............. *A61F 5/442* (2013.01); *A61F 5/441* (2013.01); *A61F 2005/4486* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,366,836 A | * | 1/1983 | Villari | A61F 5/441 137/550 |
| 4,411,659 A | | 10/1983 | Jensen | |
| D295,220 S | | 4/1988 | Kay | |
| 4,957,518 A | * | 9/1990 | Brassell | A61L 11/00 55/385.4 |
| 5,470,325 A | * | 11/1995 | Fundock | A61F 5/441 604/332 |
| 5,658,266 A | * | 8/1997 | Colacello | A61F 5/441 604/277 |
| 5,658,267 A | * | 8/1997 | Colacello | A61F 5/441 604/327 |
| 5,683,372 A | * | 11/1997 | Colacello | A61F 5/441 604/277 |
| 5,690,623 A | | 11/1997 | Lenz | |
| 6,224,581 B1 | * | 5/2001 | Withers | A61F 5/44 134/166 R |
| 6,712,800 B2 | | 3/2004 | Kanbara | |
| 7,001,367 B2 | | 2/2006 | Arkinstall | |
| D533,659 S | | 12/2006 | Conrad | |
| 7,406,963 B2 | * | 8/2008 | Chang | A61M 16/022 128/200.16 |
| 7,468,056 B2 | | 12/2008 | Burt | |
| 7,815,618 B2 | * | 10/2010 | Schena | A61F 5/4407 604/332 |
| 7,918,836 B2 | * | 4/2011 | Gill | A61F 5/445 604/332 |
| 2006/0106354 A1 | | 5/2006 | Vantroostenberghe | |

* cited by examiner

*Primary Examiner* — Todd J Scherbel
*Assistant Examiner* — Guy K Townsend

(57) ABSTRACT

The Ostomy bag with gas check valve and water bottle connection is constructed of an impermeable bag that is further defined with a tapered design. A bottom portion of the impermeable bag includes an outlet from which the contents of the impermeable bag may be selectively released. The impermeable bag also includes a stoma port on a side surface, which is adapted to make fluid connection with a stoma of an end user. The impermeable bag is further defined with a top ridge that is distally opposite of the bottom portion. Located along the top ridge of the impermeable bag is a gas check valve, and which is adjacent to a water bottle connection.

3 Claims, 7 Drawing Sheets

OSTOMY BAG WITH GAS CHECK VALVE AND WATER BOTTLE CONNECTION

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of Ostomy bags, more specifically, an Ostomy bag that is able to selectively release gas, and or wash out the interior of the Ostomy bag as needed, and in concert with the traditional function of an Ostomy bag.

Ostomy bags are prosthetic medical devices that are used to collect waste from a surgically diverted biological system. Moreover, the Ostomy bag is in fluid communication with a stoma that is formed during a surgically diverted biological system. Ostomy bags may be used to collect waste in the form of urine or fecal matter. The Ostomy bag forms a water-tight connection with the stoma so as to prevent any leakage.

Ostomy bags can become dirty after prolonged use, and cleaning can be challenging. What is needed, and what is accomplished by the disclosed device, is an improvement over traditional Ostomy bags. More specifically, an Ostomy bag that enables gas build up to be selectively released at the discretion of the user via a gas check valve that is integrated into the design of the Ostomy bag. A water bottle connection is also integrated into the construction of the Ostomy so as to enable connection of a water source that is able to wash out the interior of the Ostomy bag.

SUMMARY OF INVENTION

The Ostomy bag with gas check valve and water bottle connection is constructed of an impermeable bag that is further defined with a tapered design. A bottom portion of the impermeable bag includes an outlet from which the contents of the impermeable bag may be selectively released. The impermeable bag also includes a stoma port on a side surface, which is adapted to make fluid connection with a stoma of an end user. The impermeable bag is further defined with a top ridge that is distally opposite of the bottom portion. Located along the top ridge of the impermeable bag is a gas check valve, and which is adjacent to a water bottle connection. The gas check valve is selectively opened in order to release any gas that has accumulated inside of the impermeable bag. The water bottle connection includes a spring-loaded valve that enables a water source to be connected thereto. The water bottle connection enables water to be flushed through the interior of the impermeable bag thereby cleaning the interior of the impermeable bag, and thereafter released out the outlet located on the bottom portion.

These together with additional objects, features and advantages of the ostomy bag with gas check valve and water bottle connection will be readily apparent to those of ordinary skill in the art upon reading the following detailed description of the presently preferred, but nonetheless illustrative, embodiments when taken in conjunction with the accompanying drawings.

In this respect, before explaining the current embodiments of the ostomy bag with gas check valve and water bottle connection in detail, it is to be understood that the ostomy bag with gas check valve and water bottle connection is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the ostomy bag with gas check valve and water bottle connection.

It is therefore important that the claims be regarded as including such equivalent construction insofar as they do not depart from the spirit and scope of the ostomy bag with gas check valve and water bottle connection. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Further-more, there is no intention to be bound by any expressed or implied theory presented in the preceding technical field, background, brief summary or the following detailed description.

Figure 1:
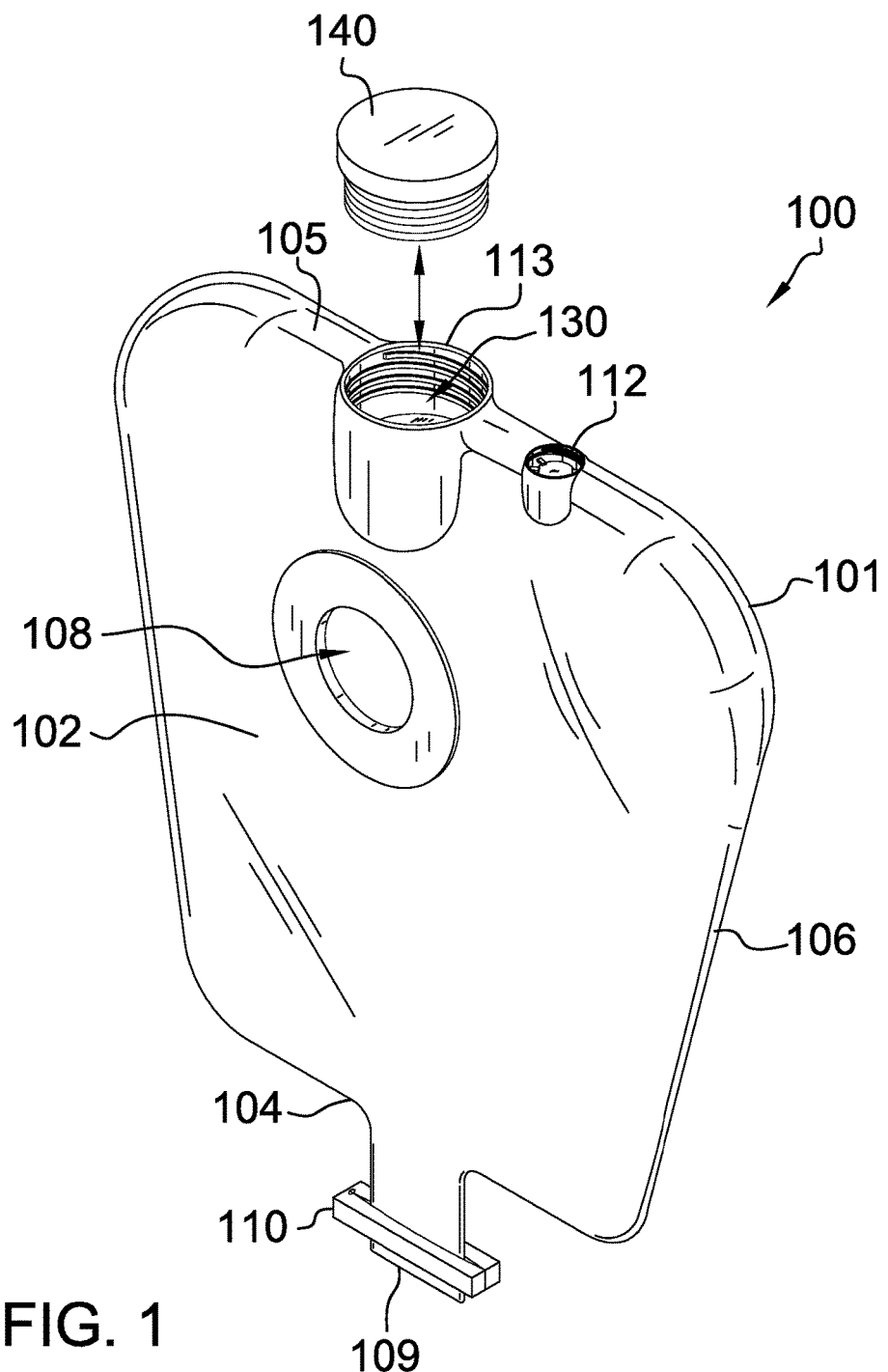
FIG. 1 is a perspective view of an embodiment of the disclosure.
Figure 2:
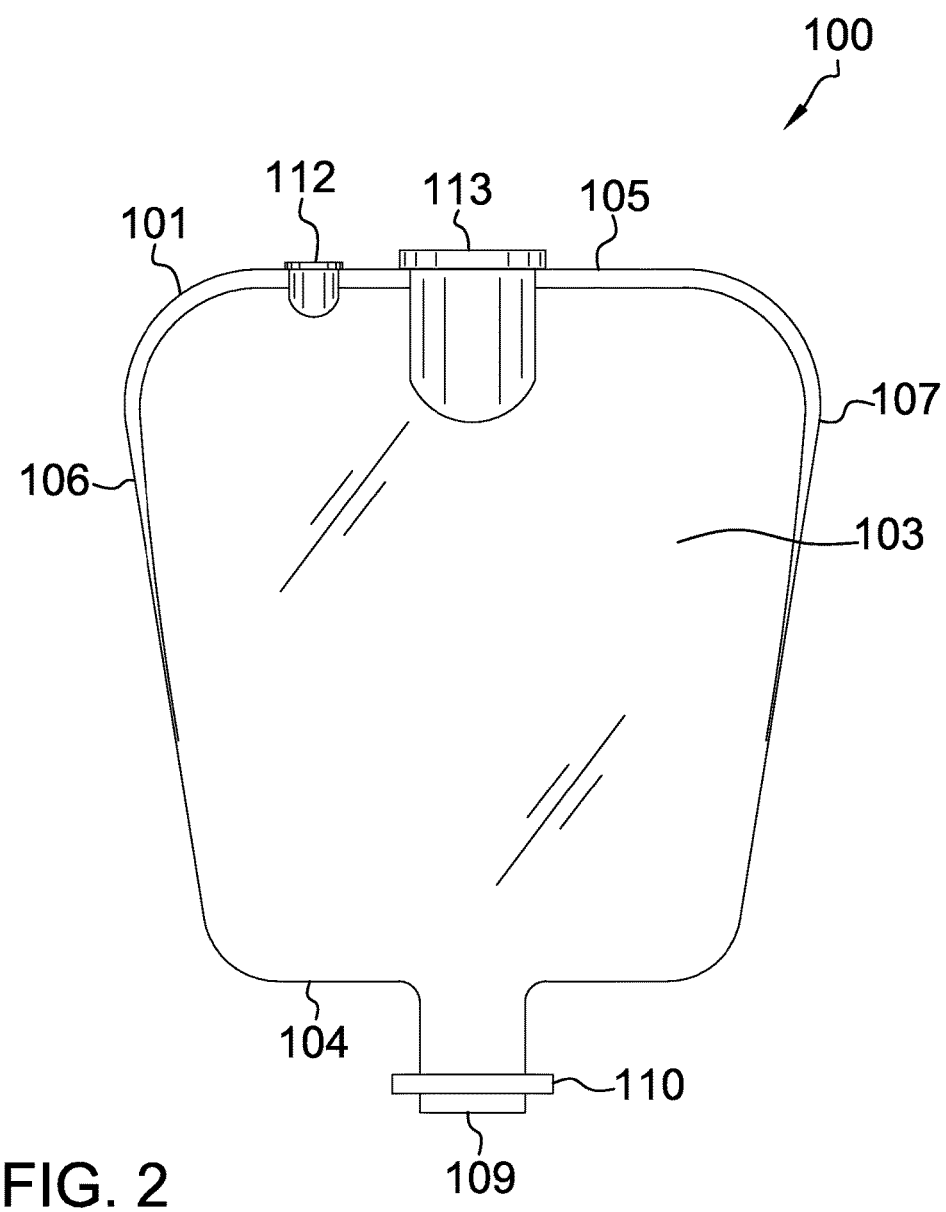
FIG. 2 is a rear view of an embodiment of the disclosure.
Figure 3:
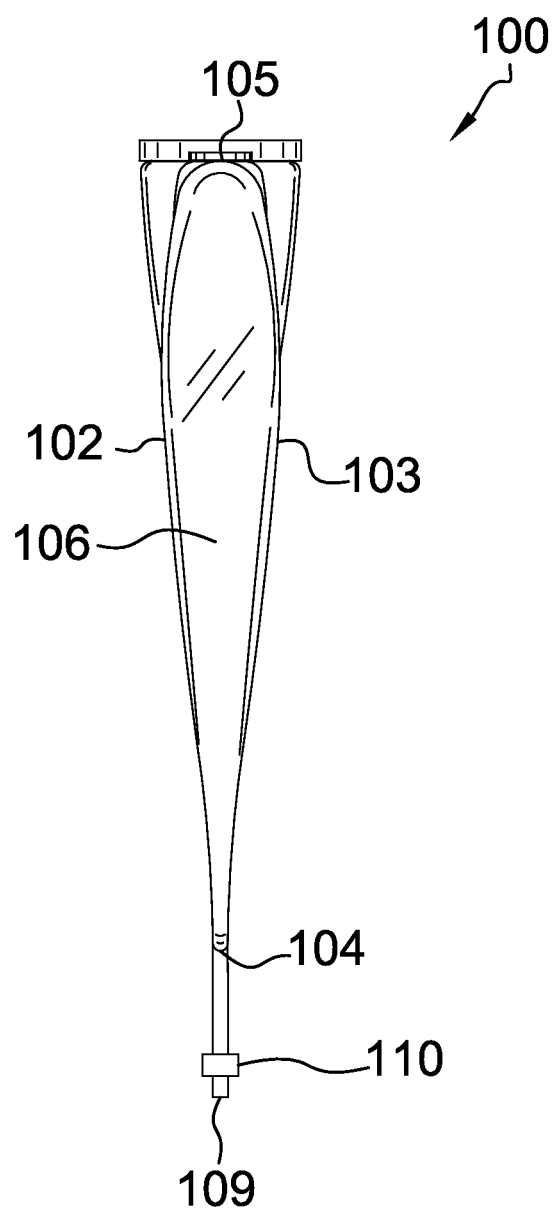
FIG. 3 is a side view of an embodiment of the disclosure.
Figure 4:
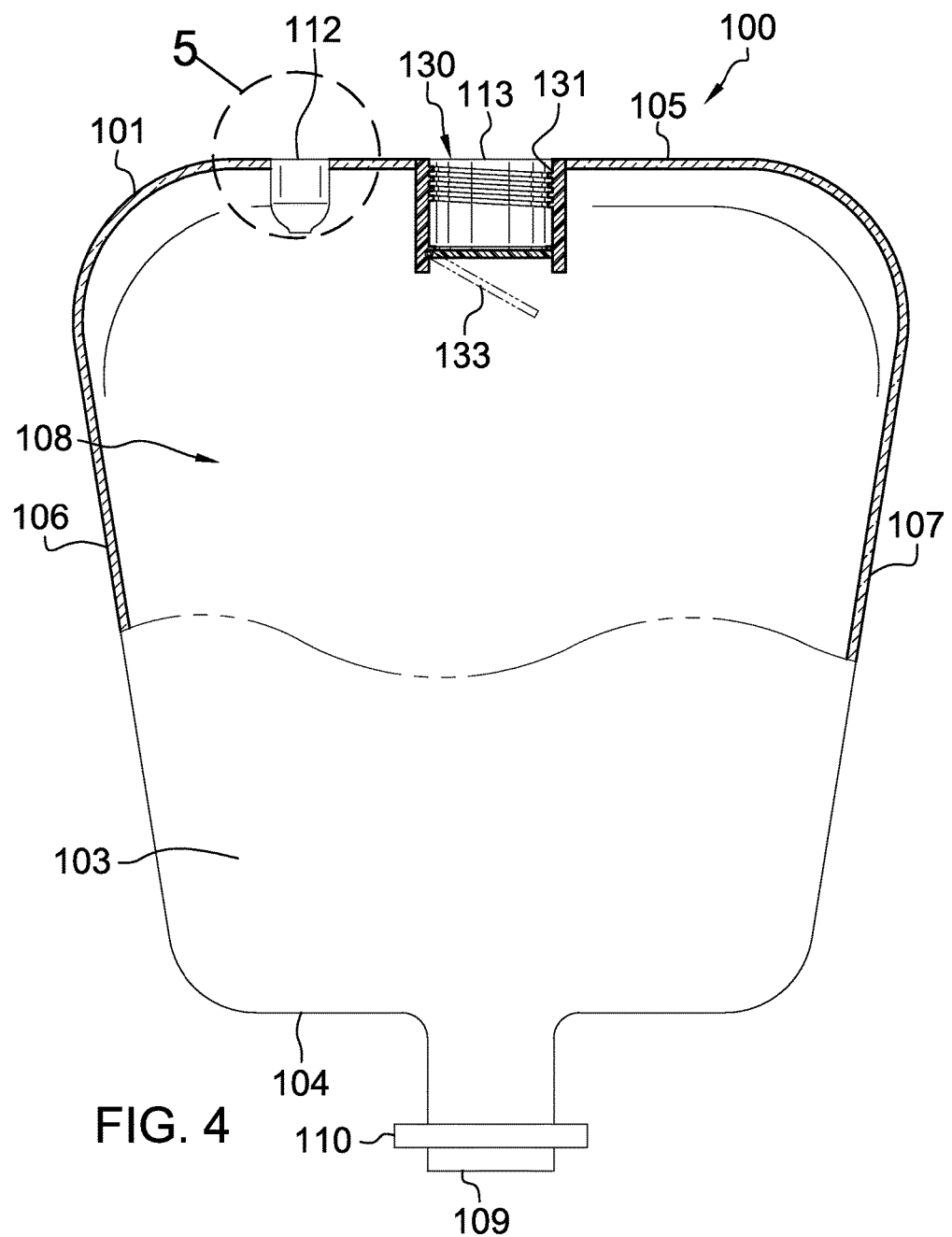
FIG. 4 is a partial cut-away rear view of an embodiment of the disclosure.
Figure 5:
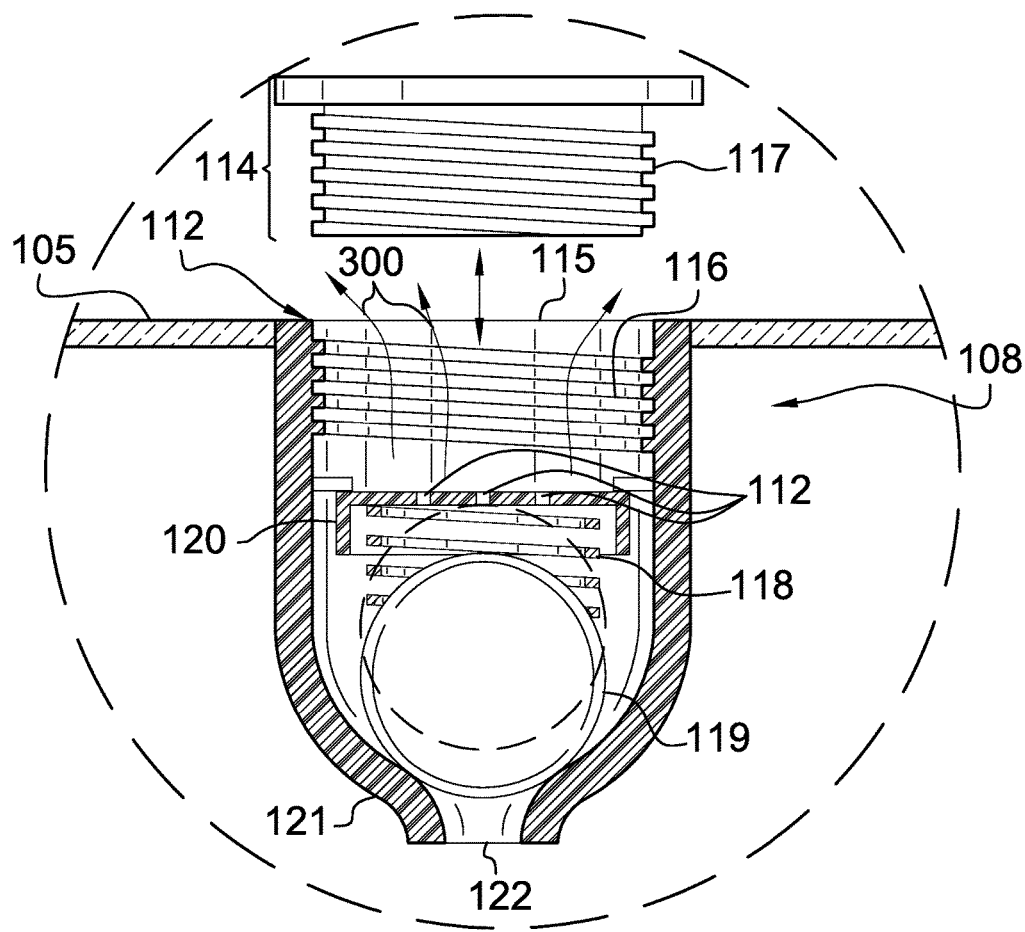
FIG. 5 is a close up detail view of an embodiment of the disclosure.
Figure 6:
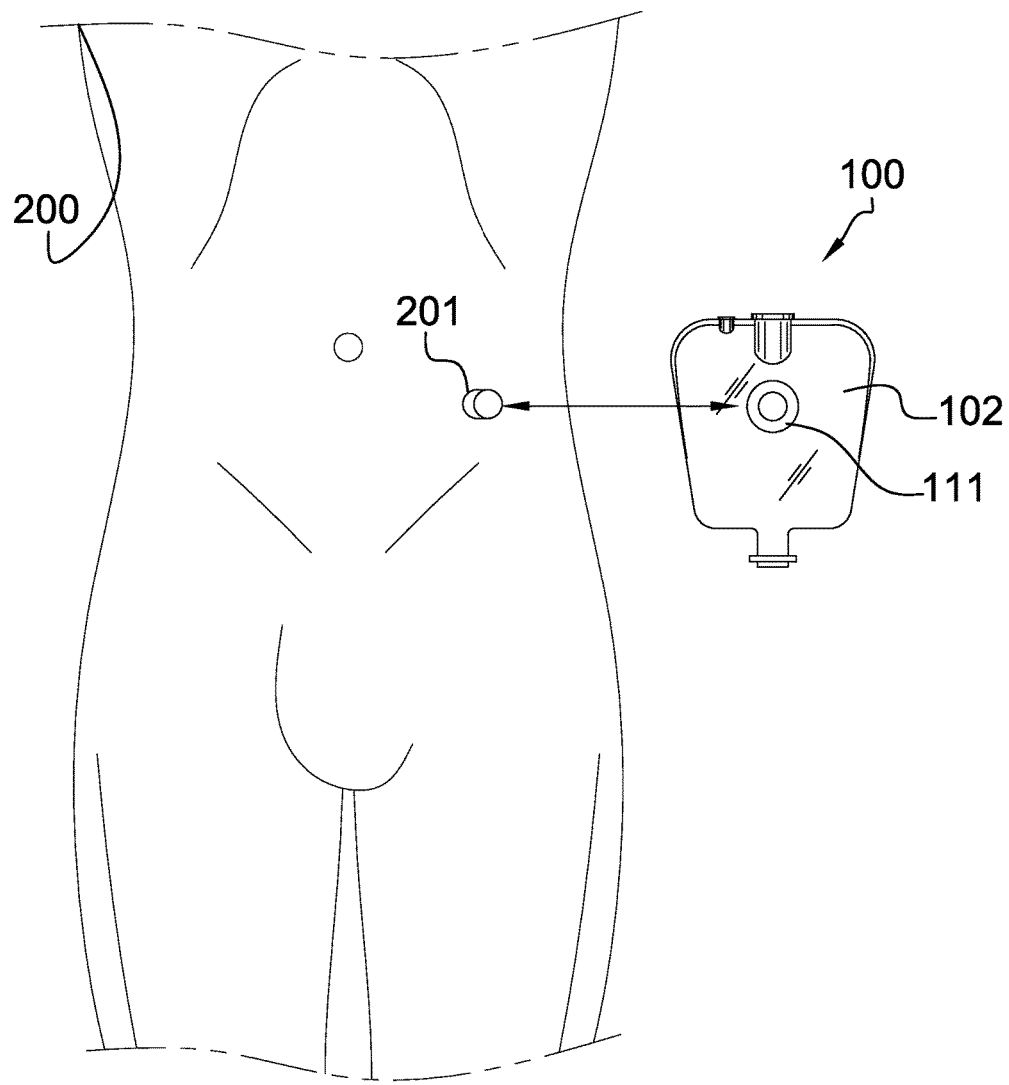
FIG. 6 is a view of an embodiment of the disclosure aligned for installation on a stoma of an end user.
Figure 7:
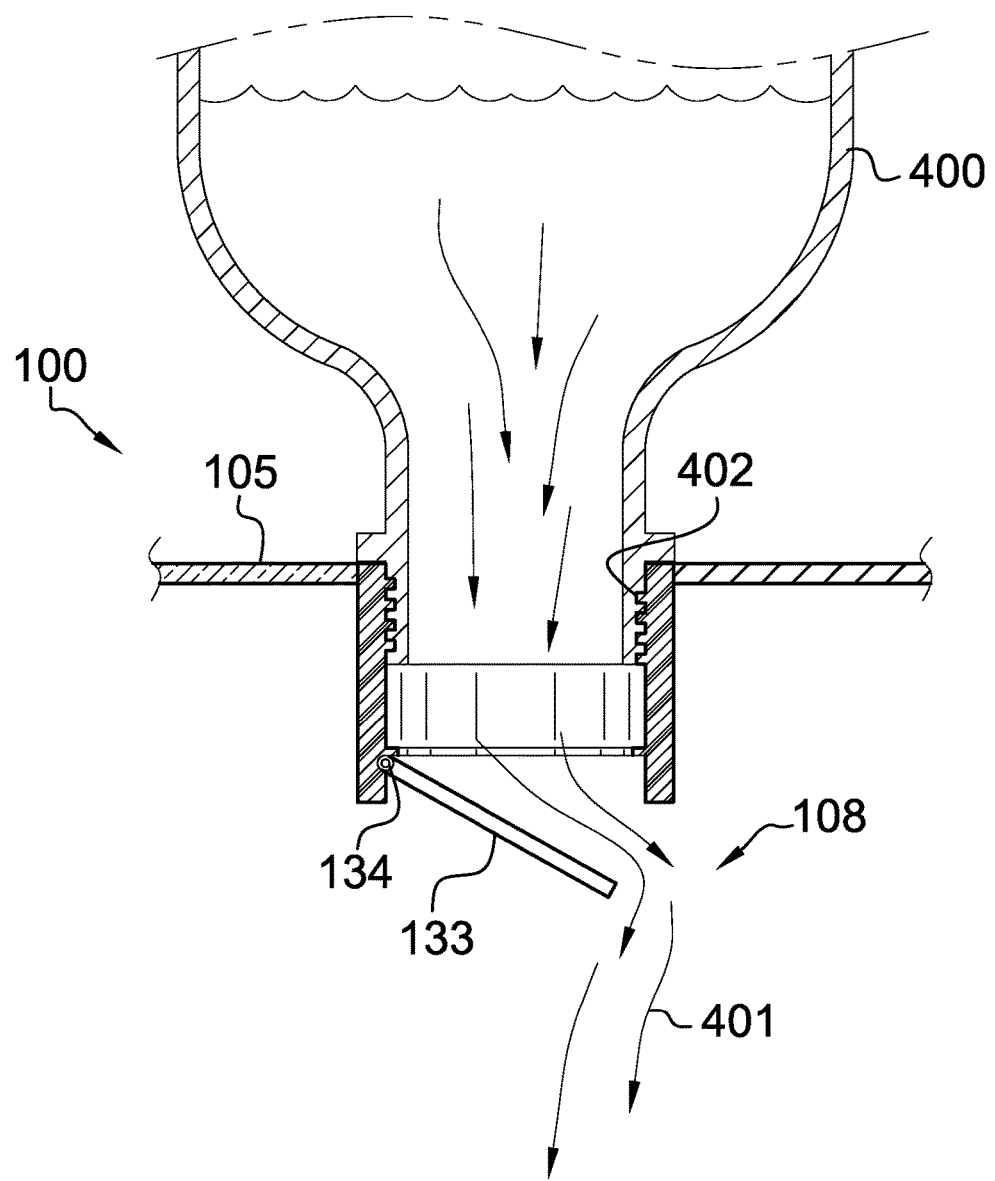
FIG. 7 is a cross-sectional view of the water bottle connection in use with a water source of an embodiment of the disclosure.

Detailed reference will now be made to a first potential embodiment of the disclosure, which is illustrated in FIGS. 1 through 7. The Ostomy bag with gas check valve and water bottle connection 100 (hereinafter invention) comprises an impermeable bag 101 that is further defined with a first side surface 102, and a second side surface 103. The first side surface 102 mirrors that of the second side surface 103. The impermeable bag 101 has a tapered design, and is also further defined with a bottom portion 104, and a top ridge 105. The bottom portion 104 is located opposite of the top ridge 105. The impermeable bag 101 may be further defined with a third surface 106 and a fourth surface 107. The third surface 106 and the fourth surface 107 are opposite one another, and may also be referred to as a left side and a right side of the impermeable bag 101. The impermeable bag 101 is also further defined with an interior 108.

The bottom portion 104 includes an outlet 109 thereon. The outlet 109 is located at a bottommost portion of the invention 100, and includes a locking clip 110 thereon. The locking clip 110 is used to selectively seal off the outlet 109. The removal of the locking clip 110 enables contents of the interior 108 of the impermeable bag 101 to be evacuated. The outlet 109 is diametrically opposite of the top ridge 105 of the impermeable bag 101.

The first side surface 102 of the impermeable bag 101 includes a stoma port 111 thereon. The stoma port 111 is well known in the art unit pertaining to Ostomy bags. Moreover, the stoma port 111 is adapted to interface with a stoma 201 of an end user 200.

The top ridge 105 includes a gas check valve 112 thereon. The gas check valve 112 is adjacent to a water bottle connection 113. The water bottle connection 113 is centrally aligned on the top ridge 105; whereas the gas check valve 112 is positioned between the water bottle connection 113 and the third surface 106 of the impermeable bag 101. It shall be noted that the gas check valve 112 and the water bottle connection 113 are flush with the top ridge 105. The gas check valve 112 is included with the invention 100 for the purpose of selectively releasing gas that may build up inside of the impermeable bag 101. The gas check valve 112 includes a gas check plug 114 that is screwed onto a first top opening 115 provided on the gas check valve 112. The gas check plug 114 is unscrewed in order for accumulated gas 300 to be expelled via the gas check valve 112.

The first top opening 115 includes internal threads 116 that correspond with external threads 117 provided on the gas check plug 114. The interior of the gas check valve 112 includes a spring member 118 positioned between a check ball 119 and a spring stop 120. The gas check valve 112 includes a graduated housing 121 that supports the check ball 119 as well as the spring stop 120 and the spring member 118. The gas check valve 112 is further defined with a check valve inlet 122 that is located in the interior 108 of the impermeable bag 101. As gas 300 accumulates in the interior 108 of the impermeable bag 101, the check ball 119 is pushed upwardly towards the spring stop 120 in order for gas 300 to enter through the check valve inlet 122.

Assuming the gas check plug 114 is removed, said gas 300 is able to pass across the spring stop 120, and exit the first top opening 115 of the gas check valve 112. It shall be noted that the spring stop 120 includes at least one stop hole 123 thereon, which enables gas 300 to pass across the check valve inlet 122 to the first stop opening 115.

The water bottle connection 113 is a component of the invention 100 that enables a water source 400 to be in fluid communication with the impermeable bag 101. Moreover, the water source 400 is used to introduce water 401 into the interior 108 of the impermeable bag 101 in order to wash out the interior 108 of the impermeable bag 101. It shall be noted that the water source 400 is subsequently evacuated via the outlet 109 located at the bottom portion 104 of the impermeable bag 101. The design of the relative locations of the outlet 109 and the water bottle connection 113 is on purpose in that the use of gravity assists in the fluid flow of the water 401 from the top right 105 down to the bottom portion 105. Also, the located of the gas check valve 112 adjacent the water bottle connection 113 insures that the gas check valve 112 is able to operate normally during use of the water bottle connection 113.

The water bottle connection 113 is adapted for use with a water source 400. It shall be noted that the water source 400 may or may not involve the use of an actual water bottle. However, the water bottle connection 113 includes a water inlet with a third internal threading 131 that corresponds with a water source external threading 402 in order to ensure a watertight connection there between. The water bottle connection 113 includes a spring-loaded flapper valve 133 that is located below the third internal threading 131. The spring-loaded flapper valve 133 is seated in a closed position via a flapper spring 134. The spring-loaded flapper valve 133 is unseated when the water bottle connection 113 is attached to the water source 400, and water 401 is being transferred from the water source 400 into the interior 108 of the impermeable bag 101. The water bottle connection 113 may include a water connection plug 140 that is screwed onto the water inlet 130 via the third internal threading 131. The use of the water connection plug 140 is used between cleaning of the impermeable bag 101.

With respect to the above description, it is to be realized that the optimum dimensional relationship for the various components of the invention described above and in FIGS. 1 through 7, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

Is shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An Ostomy bag with a gas check valve and a water bottle connection comprising
    an impermeable bag that is adapted to attach to a stoma of an end user;
    wherein the impermeable bag includes an outlet for evacuation of contents collected inside of said impermeable bag;
    wherein the impermeable bag includes a water bottle connection in order to adaptively connect a water source, which introduces water into an interior of the impermeable bag in order to wash out said interior of the impermeable bag, and said water thereafter being evacuated via the outlet of said impermeable bag;

wherein the impermeable bag is further defined with a first side surface, and a second side surface;

wherein the first side surface mirrors that of the second side surface;

wherein the impermeable bag has a tapered design, and is also further defined with a bottom portion, and a top ridge;

wherein the bottom portion is located opposite of the top ridge;

wherein the impermeable bag is further defined with a third surface and a fourth surface;

wherein the third surface and the fourth surface are opposite one another;

wherein the bottom portion includes the outlet thereon;

wherein the outlet is located at a bottommost portion of the impermeable bag, and includes a locking clip thereon;

wherein the locking clip is used to selectively seal off the outlet;

wherein the removal of the locking clip enables contents of the interior of the impermeable bag to be evacuated;

wherein the outlet is diametrically opposite of the top ridge of the impermeable bag;

wherein the first side surface of the impermeable bag includes a stoma port thereon;

wherein the stoma port is adapted to interface with the stoma of the end user;

wherein the top ridge includes the gas check valve thereon;

wherein the gas check valve is adjacent to the water bottle connection;

wherein the water bottle connection is centrally aligned on the top ridge;

wherein the gas check valve is positioned between the water bottle connection and the third surface of the impermeable bag;

wherein the gas check valve and the water bottle connection are flush with the top ridge;

wherein the gas check valve selectively releases gas that builds up inside of the impermeable bag;

wherein the gas check valve includes a gas check plug that is screwed onto a first top opening provided on the gas check valve;

wherein the gas check plug is unscrewed in order for accumulated gas to be expelled via the gas check valve;

wherein the first top opening includes internal threads that correspond with external threads provided on the gas check plug;

wherein the interior of the gas check valve includes a spring member positioned between a check ball and a spring stop;

wherein the gas check valve includes a graduated housing that supports the check ball as well as the spring stop and the spring member;

wherein the gas check valve is further defined with a check valve inlet that is located in the interior of the impermeable bag;

wherein as gas accumulates in the interior of the impermeable bag, the check ball is pushed upwardly towards the spring stop in order for gas to enter through the check valve inlet;

wherein once the gas check plug is removed, said gas is able to pass across the spring stop, and exit the first top opening of the gas check valve;

wherein the spring stop includes at least one stop hole thereon, which enables gas to pass across the check valve inlet to the first stop opening;

wherein the relative locations of the outlet and the water bottle connection is such that gravity assists in the fluid flow of the water from the top ridge down to the bottom portion;

wherein the water bottle connection includes a water inlet with a third internal threading that corresponds with a water source external threading in order to ensure a watertight connection there between.

2. The Ostomy bag with the gas check valve and the water bottle connection according to claim 1 wherein the water bottle connection includes a spring-loaded flapper valve that is located below the third internal threading; wherein the spring-loaded flapper valve is seated in a closed position via a flapper spring; wherein the spring-loaded flapper valve is unseated when the water bottle connection is attached to the water source, and water is transferred from the water source into the interior of the impermeable bag.

3. The Ostomy bag with the gas check valve and the water bottle connection according to claim 2 wherein the water bottle connection includes a water connection plug that is screwed onto the water inlet via the third internal threading; wherein the water connection plug is used between cleanings of the impermeable bag.

* * * * *